United States Patent [19]

Kato et al.

[11] Patent Number: 4,686,453

[45] Date of Patent: * Aug. 11, 1987

[54] OIL MIST DETECTION METHOD AND APPARATUS

[75] Inventors: Takayuki Kato, Aichi; Makoto Miyamoto, Kariya, both of Japan

[73] Assignee: Aisin Seiki Kabushiki Kaisha, Aichi, Japan

[*] Notice: The portion of the term of this patent subsequent to Aug. 11, 2004 has been disclaimed.

[21] Appl. No.: 795,180

[22] Filed: Nov. 5, 1985

[30] Foreign Application Priority Data

Nov. 5, 1984 [JP] Japan ................ 59-233850

[51] Int. Cl.$^4$ ............................................. G01R 27/02
[52] U.S. Cl. ................................. 324/65 R; 73/116
[58] Field of Search ............... 73/116; 324/65 R, 65 P

[56] References Cited

U.S. PATENT DOCUMENTS

| | | | |
|---|---|---|---|
| 2,930,015 | 3/1960 | Blumer | 324/65 R |
| 2,994,821 | 8/1961 | Dravnieks | 324/65 R |
| 3,731,187 | 5/1973 | Hausler et al. | 324/65 R |
| 4,080,564 | 3/1978 | Nitta et al. | 324/65 R |
| 4,475,382 | 10/1984 | Frank | 73/116 |

FOREIGN PATENT DOCUMENTS

| | | | |
|---|---|---|---|
| 079876 | 6/1972 | Japan | 324/65 R |
| 0124515 | 7/1983 | Japan | 324/65 R |

*Primary Examiner*—Stewart J. Levy
*Assistant Examiner*—Robert R. Raevis
*Attorney, Agent, or Firm*—Oblon, Fisher, Spivak, McClelland, & Maier

[57] ABSTRACT

Method and apparatus for detection of oil mists in which oil mists in a noninflammable gas an formed into deposits by heat decomposition, an accumulated amount of the deposit is detected as a variation of electric resistance, and the amount of oil mists is detected from the electric resistance value. The apparatus includes a power source for energizing a heating member, a circuit for detection of an electric resistance between electrodes, and a display circuit for indicating an output of the detection circuit as an amount of oil mists.

4 Claims, 6 Drawing Figures

OIL MIST DETECTION METHOD AND APPARATUS

BACKGROUND OF THE INVENTION

1. Field of the Invention

The present invention relates to a method for detection of oil mist and apparatus therefor in which an oil mist in a noninflammable gas is formed into a deposit form by heat decomposition, an accumulated amount of the decomposed deposit is detected as an electric resistance variation, and the oil mist amount is detected from the electric resistance value.

2. Description of the Prior Art

Recently, a sealed reciprocating engine such as a Stirling engine is provided with a seal portion so that a cylinder having a piston slidably encased therein is sealed relative to a guide rod for transmitting a reciprocating motion of the piston outside the cylinder, and oil is used in the seal portion. This gives rise to a problem in that oil leaked from the seal portion is atomized to contaminate the interior of the cylinder to impede the reciprocating motion of the piston. It is therefore necessary to measure the oil mist within the cylinder during the reciprocating motion of the piston.

A conventional measuring device has used a piezoelectric element as an oil mist measuring sensor, for example, such as a piezo-balance dust meter. For this reason, it is not possible to arrange the device within the cylinder in which pressure is varied to directly measure the oil mist. In other words, the gas within the cylinder is subjected to sampling to make pressure constant, after which the mist is indirectly measured in a chamber separately from the cylinder. This poses disadvantages that the measuring accuracy is not obtained and a pipe for sampling is required to unavoidably increase the size of the measuring device.

A specific embodiment of prior art will be described hereinafter with reference to the drawings.

FIG. 6 shows a Stirling engine 10 which converts energy of a high temperature and high pressure gas into a turning force. Four cylinders 11 (including those not shown) are symmetrically provided. Each cylinder 11 has a piston 12 arranged therein, and an expansion chamber 13 and a compression chamber 14 are formed on opposite ends, respectively, thereof. The expansion chamber 13 and compression chamber 14 are communicated with heat exchangers 15a and 15b, respectively, which are working as gas supply sources.

Each piston 12 has a guide rod 16 to transmit a reciprocating motion of the piston 12 outside the cylinder 11 through a rod seal 17. The guide rod 16 has a guide piston 18 connected thereto which is slidably moved within a guide cylinder 19. Each guide piston 18 is brought into engagement with a rotational oblique swash plate 20, which has a rotational shaft 21.

A helium gas is supplied to the engine 10 constructed as described above, and the piston 12 is periodically reciprocated within the cylinder 11.

This reciprocating motion is transmitted through the guide rod 16, and the guide pistons 18 are also reciprocated with a predetermined phase difference from each other. With this, the rotational oblique plate 20 in engagement with the guide piston 18 is rotated, which rotation is transmitted outside through the rotational shaft 21.

Hereinafter, the construction of the rod seal 17 for maintaining the cylinder 11 airtight relative to the guide rod 16 will be described with reference to FIG. 6.

Around the guide rod 16 are arranged a gas seal 26, an intermediate chamber 25 in communication with the compression chamber 14, an oil scraper 22, a liquid chamber 23 and an oil seal 24 in that order from the compression chamber 14. The liquid chamber 23 is brought into communication with the top of the oil scraper 22 through an oil tank 27.

Since oil is used for the purpose of sealing, oil in the liquid chamber 23 possibly leaks into the compression chamber 14 through the oil scraper 22, the intermediate chamber 25 and the gas seal 26. Therefore, in the engine 10, oil is distributed in the form of mist into the compression chamber 14.

This oil mist is adhered to inner walls of pipes of the heat exchanger 15a through a pipe which connects oil on the heat exchanger 15a with the compression chamber 14. As a result, the inner walls of the pipe becomes decomposed due to the high temperature of the heat exchanger 15a.

As the oil mist accumulates on the inner walls of the pipe, a gas flowpassage of the pipe is naturally blocked to deteriorate the efficiency of heat exchange of He gas or the like and to cause the efficiency of the compressor itself to be deteriorated.

Furthermore, when the efficiency of a filter 28 deteriorates, the oil mist is distributed in the form of a mist into the compression chamber 14 through the oil scraper 22, the intermediate chamber 25 and the filter 28, in a manner similar to that as previously described.

In view of the foregoing, it is important to detect concentration of the oil mist within the compression chamber 14 for the purpose of maintaining the performance of the engine 10.

SUMMARY OF THE INVENTION

It is therefore an object of the present invention to use a small-sized detection device for which in measurement of an oil mist amount, the mist is heat-decomposed on the high temperature heater surface into a decomposed deposit form in the atmosphere of said mist so as to detect the produced amount of the deposit as an electric resistance variation, thereby enabling the direct measurement of the oil mist amount within the cylinder to overcome those disadvantages noted above.

According to the present invention, there is provided an oil mist detection method which comprises adhering an oil mist in a noninflammable gas to a sensor forming the oil mist into a deposit by heat decomposition, detecting an accumulated amount of the deposit as an electric resistance variation, and detecting the oil mist amount from the electric resistance value.

According to the present invention, there is further provided an oil mist detection apparatus comprising a heat generating member to which an oil mist in a noninflammable gas may be adhered, said member being coated with an insulating and heat-resisting element, and a pair of electrodes provided on the coating of said heat generating member, characterized in that the oil mist adhered onto the coating of said heat generating member is decomposed on said coating by heat generation of said member into a deposit form, and the oil mist amount is detected from an electric resistance variation between said electrodes corresponding to the deposit amount accumulated on said coating.

In accordance with the present invention, it is possible to very easily measure the concentration of oil mist according to the variation of surface resistance of a small-sized heater in the oil mist in the cylinder.

With this, there result the excellent effects that the oil mist amount in the cylinder can be measured directly without being affected by the variation in pressure in the cylinder, and that where the gas in the cylinder is subjected to sampling to measure the oil mist amount, it is possible to very easily and accurately determine the oil mist condition in the cylinder.

DETAILED DESCRIPTION OF THE INVENTION AND PREFERRED EMBODIMENTS

If the oil mist detection means according to the present invention is mounted on a portion A in the compression chamber 14 of the engine 10 or on a portion B between the filter 28 and the compression chamber 14, the concentration of oil mist may be always monitored.

Figure 6:
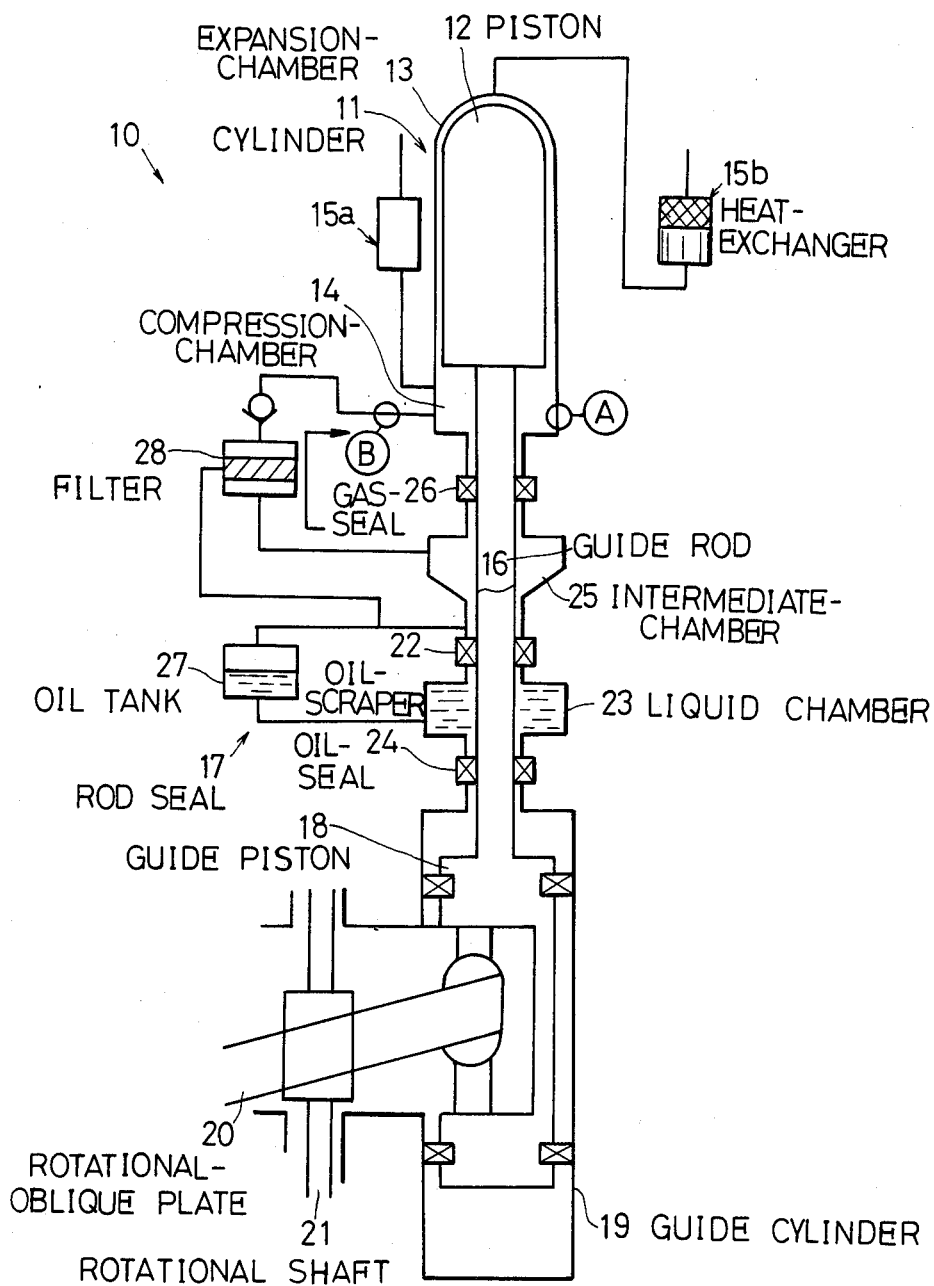
FIG. 6 is an illustration of the engine shown as a prior art.

In the following, a preferred embodiment of detection of oil mist that may be mounted on the portion A and the portion B of the engine 10 shown in FIG. 6 will be described with reference to the drawings.

Figure 2:
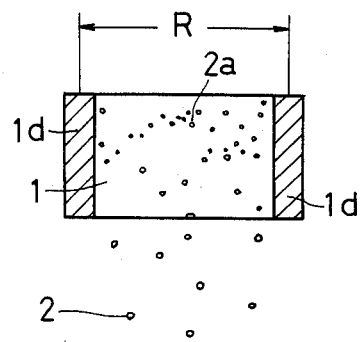
FIG. 2 shows a principle component of the oil mist sensor of the present invention.

FIG. 2 shows the operating principle of the oil mist detection means according to the present invention.

The compression chamber of the engine is filled with helium gas, which is compressed.

Accordingly, since oxygen is not present within the compression chamber, the oil mist is never burned but decompose. The operating principle of the oil mist detection means according to the present invention makes use of the aforesaid atomosphere to decomposed the oil mist on the high-temperature heater surface without combustion of the oil mist to form it into a heat-decomposed deposit form.

In FIG. 2, when oil mists 2 are adhered to the surface of a mist sensor 1 heated to a high temperature, the oil mists are decomposed on the surface of the sensor 1 to form a deposit 2a whose main component is carbon.

If the sensor 1 comprises a ceramic heater or the like, in the event that no deposit 2a is present on the surface thereof, resistance R between electrodes 1d is infinite.

Figure 3:
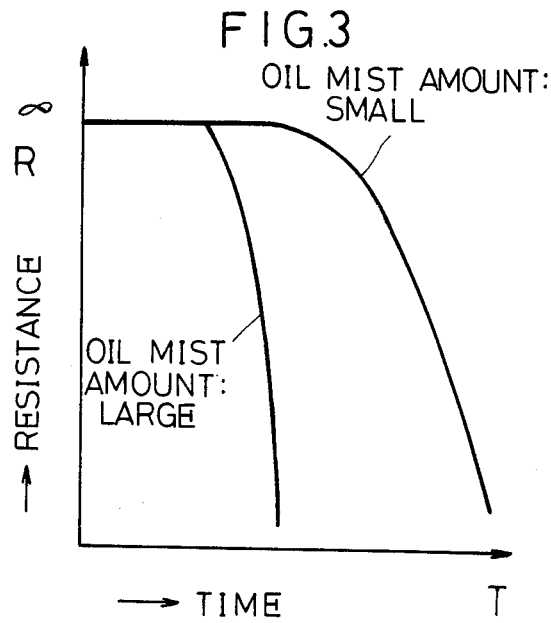
FIG. 3 is a diagram showing the resistance R between the two electrodes in relation to the amount of the oil mist deposits.

However, as the deposits 2a are accumulated on the reduced surface by decomposing the mists 2, the resistance R between the electrodes 1d decreases as shown in FIG. 3 owing to the resistance of the deposits themselves.

Since a principal component of the oil is hydrocarbon, the oil mists are also of the same composition.

Thus, when the oil mists are adhered onto the surface of the sensor 1, and changed into a deposit form, the resistance R between the electrodes 1d decreases due to the conductivity of the deposit.

In the oil mist sensor according to the present invention, the surface temperature of the sensor suitable for changing the oil mist in the helium gas into a decomposed deposit form is of the order of 750° to 900° C. This is the temperature required in order that hydrocarbon contained in the oil mist may be formed into a deposit.

However, black deposits formed by forming the oil mists into deposits which are then accumulated on the sensor surface contain, in addition to carbon, sulphur, phosphorus and various additives. Since these elements are very small in quantity, a principal component of the deposits 2a on the sensor surface is mostly carbon, i.e. sintered carbide, and is electrically conductive. Thus, as shown in FIG. 2, if the mist is present, the resistance R between the electrodes 1d of the sensor 1 gradually decreases from an infinite value, and the rate of decrease thereof varies with the concentration of mist.

Next, a specific embodiment of the mist sensor 1 as a detection apparatus according to the present invention will be described with reference to FIG. 1.

A mist sensor 1 comprises a substrate 1a formed of ceramic or the like which is excellent in insulating and heat resisting properties, a heating wire 1b formed of a nichrome wire or a kanthal wire wound around the substrate 1a, a coating 1c such as ceramic sintered on the heating wire 1b and on the outer surface of the substrate 1a, and electrodes 1d provided on opposite ends of the coating 1c. The heating wire 1b and the electrodes 1d are respectively connected to terminals 1e of a socket 1f formed of a material which is excellent in insulating and heat resisting properties, and may be connected to external circuits through pin terminals 1g.

With the above-described construction, when the heating wire 1b is energized by an external power source, the heating wire 1b is heated so that the surface of the coating 1c is heated to 750°–900° C. Under this heating condition, if oil mists are present in the atmosphere of helium gas in the compression chamber of the compressor, the mists are decomposed on the coating 1c to form deposits. When the deposits are accumulated, the surface of the insulating coating 1c becomes conductive to decrease the resistance between the electrodes 1d of the sensor 1. The variation of resistance between the electrodes 1d may be measured by the external circuit through the pin terminals 1g.

The deposits decomposed onto the surface of the coating 1c of the sensor 1 indicate the integrated value of mist concentration since they are accumulated according to the time and mist concentration. Accordingly, if the relationship between the mist concentration, time and resistance is determined before hand, it is possible to detect the oil mist concentration from the value of the resistance R between the electrodes of the sensor 1. It is possible to know whether the oil mist concentration is at a set value by setting a reference value with respect to the resistance R, that is, by comparing a measured value of R with a value for a known mist concentration.

Figure 4:
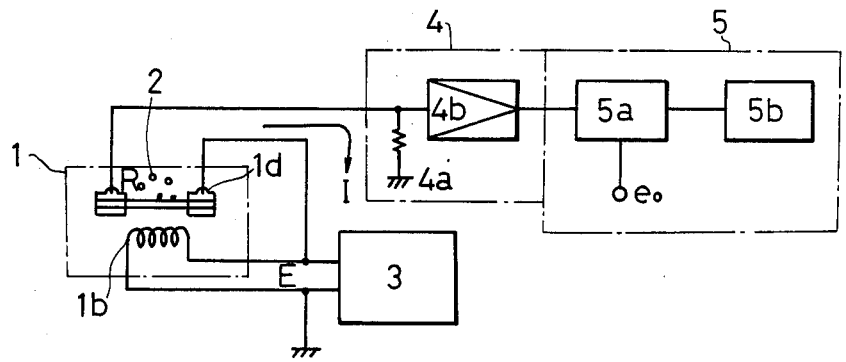
FIG. 4 shows a specific embodiment of an oil mist detection apparatus making use of the sensor.

FIG. 4 shows a specific embodiment of an oil mist detection apparatus making use of the sensor 1.

The oil mist detection apparatus comprises the oil mist sensor 1 described in connection with FIG. 1, power source means 3 connected to the heating wire 1b of the sensor 1 to heat the heating wire 1b and connected to one of the electrodes 1d of the sensor 1, detection circuit means 4 connected to the other of the electrodes 1d of the sensor 1 to measure the resistance between the electrodes of the sensor 1, and display means 5 which receives output of the detection circuit means 4 to display abnormality or the like of the oil mist amount. In the oil mist detection device constructed as described above, when the heating wire 1b of the sensor means 1 is energized to be heated by the power source means 3, the oil mists 2 are decomposed on the surface of the sensor 1 to form deposits. The deposits on the surface of the sensor accumulate as conductive materials between the electrodes 1d of the surface of the sensor. When a fixed voltage E is applied between the electrodes 1d of the sensor surface from the power supply means 3, an electric current I flows through the deposits, and flows into the detection circuit means 4 through the other electrode 1d.

Accordingly, in the detection circuit means 4, if the current I flowing through the deposits on the surface of the sensor is measured, the resistance of the deposits, that is, the resistance R in the form of the integrated value of the oil mist amount can be measured by $R = E/I$ in accordance with Ohm's law.

More specifically, the current I flowing between the electrodes 1d of the sensor 1 is converted into a voltage signal by a load resistor 4a and a voltage detection circuit 4b.

Next, the display means 5 comprises a judgment circuit 5a and a display circuit 5b. Output of the detection circuit means 4 is put into the judgment circuit 5a. The judgment circuit 5a compares the output with a reference value Eo obtained before hand for a normal mist concentration value. When, the output value of the detection circuit means 4 exceeds the reference value Eo, the display circuit 5b displays that the oil mist amount is abnormal.

It is to be noted that in the display means 5, output of the detection circuit means 4 is displayed without modification on an analog meter, and OK (acceptable) and NG (no good) zones of the oil mist amount can be provided on the analog meter.

In the following, another embodiment of the sensor means 1 in connection with the oil mist sensor will be described with reference to FIG. 5.

Figure 1:
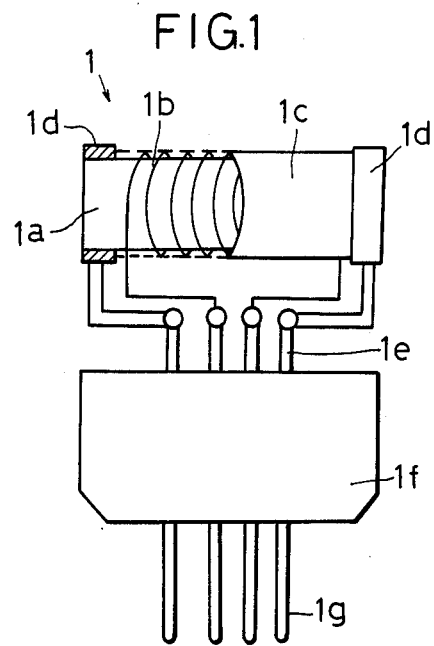
FIG. 1 is a schematic view showing a specific embodiment of an oil mist sensor of the present invention.

Parts having the same effects as those of the sensor means 1 described in connection with FIG. 1 are indicated by the same reference numerals.

Figure 5:
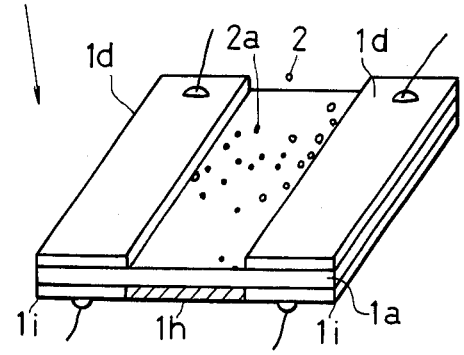
FIG. 5 shows the other preferred embodiment of the oil mist sensor.

Referring to FIG. 5, the sensor means 1 comprises a pair of electrodes 1d provided on one surface of a substrate 1a formed of an insulating and heat resisting material such as ceramic, a surface heating member 1h such as a ceramic heater or a film heater provided on the other surface of the substrate 1a, and a pair of electrodes 1i for energizing the surface heating member. With the sensor means 1 constructed as described above, when the substrate 1a is heated by the surface heating member 1h, oil mists adhered onto the substrate 1a are decomposed to form deposits. The amount of the deposits 2a formed from the oil mists can be detected as the resistance between the electrodes 1d.

With this arrangement, since the sensor means can be formed into an extremely thin and small-sized configuration, the oil mists may be decomposed by means of a heater of low heat capacity.

In the oil mist sensor constructed as described above, if the oil mist adhered to surfaces of the coating 1c in FIG. 1 and the substrate 1a in FIG. 5 of said sensor means 1 are formed of ceramic material having porous or coarse particles, the mist may be adhered, decomposed and deposited efficiently.

While in FIGS. 1 and 5, the sensor means 1 is in the shape of a flat plate, it is to be understood that a cylindrical shape, a rod-like shape or other suitable shapes may be employed.

In the sensor means 1 shown in FIG. 1, if the heating wire 1b is formed from a nichrome wire to form a heater having a capacity of approximately 5 watts, the surface temperature of the coating 1c is set to approximately 850° C. (red hot state). If oil mists of several thousand ppm are generated in the helium gas atmosphere by the operation of said steering engine, then the resistance between the electrodes 1d of the sensor means 1 decreases to a few K ohm in a few hours from the infinite value, as found from the experimental results. The oil mists may be detected efficiently and with high sensitivity according to the area, shape and the like of a film of the sensor means 1.

The important point of the oil mist sensor lies in setting a temperature at which the oil mists may be decomposed on the surface of the sensor means 1 to form deposits.

It has been found from several experiments that the optimum temperature for decomposing of the oil mists in this sensor is from 750° to 900° C. The size of the sensor means 1 and the heating capacity may be determined so that to assume the range of temperature as described. The detection sensitivity of the oil mists may be suitably varied by varying the surface temperature of the sensor means 1.

The sensor has the following significant features. That is, deposits in which oil mists are decomposed on the surface of the sensor can be self-cleaned if exposed to air. The deposits are decomposed on the sensor means 1 in the following step:

Oil mists→in-helium gas→deposits of hydrocarbon are decomposed on the heater surface at 850° C.

The deposits on the sensor surface comprise a carbon as a principal component, and therefore the deposits can be burned in air. That is to say,

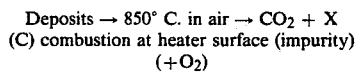

Deposits → 850° C. in air → $CO_2$ + X
(C) combustion at heater surface (impurity)
(+$O_2$)

Thus, the deposits on the sensor surface burn off and can be removed and cleaned in air.

As the result of the foregoing, the excellent characteristic is provided: Where the oil mist sensor detects abnormality of the oil mists and the oil mist detection apparatus is actuated, if the sensor means is actuated in air after the abnormal places of the engine have been corrected, the deposits decomposed on the sensor surface can be burned at its own heating temperature to remove the same, thus facilitating reuse of the sensor.

While the description has been made of the embodiment in which the oil mist sensor is applied to the engine, it is to be understood that the sensor can be applied also to detect oil mists in an extremely low-temperature freezer which uses a noninflammable gas such as helium gas.

It will be further noted that the atmosphere applied to the oil mist sensor can be any noninflammable gas such as helium gas and under which the surface temperature of the sensor is maintained at 750° to 900° C. Pressure and temperature in the atmosphere is affected at minimum.

Moreover, the heater can be formed to have a capacity of 3 to 5 W. The sensor itself is of an extremely small and simple construction and can be directly mounted in a compression chamber of a freezer, a compressor or the like, thus performing a significant role in maintaining the performance thereof.

What is claimed is:

1. An oil mist detection method which comprises the steps of:

permitting an oil mist in an inert gas to adhere onto a surface of an insulating body, forming the adhered oil mist into a conductive carbon deposit by heat decomposition, detecting an accumulated amount of the deposit as a variation of an electric resistance through said deposit, and detecting a concentration of said oil mist in said gas from a value of said electric resistance.

2. An oil mist detection apparatus comprising:

a heat generating member disposable in an inert gas having an oil mist therein, whereby said oil mist is adhered thereto, said member being coated with an insulating and heat-resisting coating, a pair of electrodes provided on the coating of said heat generating member, wherein said oil mist adhered onto the coating of said heat generating member is decomposed on said coating by heat generated in said member into a decomposed conductive carbon depositform, and means for detecting a concentration of said oil mist in said gas as a decrease of electric resistance between said electrodes, said decrease corresponding to the amount of said deposit accumulated on said coating.

3. An oil mist detection apparatus according to claim 2, including a power source for energizing and heating said heat generating member, and a display circuit for displaying an output of said detecting means as said oil mist concentration.

4. An oil mist detection apparatus according to claim 2, wherein said coating of said heat generating member comprises a ceramic of coarse particles.

* * * * *